US009905001B2

(12) United States Patent
Ikeda

(10) Patent No.: US 9,905,001 B2
(45) Date of Patent: Feb. 27, 2018

(54) IMAGE PROCESSING APPARATUS AND IMAGE PROCESSING METHOD

(71) Applicant: TOSHIBA MEDICAL SYSTEMS CORPORATION, Otawara-shi (JP)

(72) Inventor: Yoshihiro Ikeda, Sakura (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 108 days.

(21) Appl. No.: 14/944,496

(22) Filed: Nov. 18, 2015

(65) Prior Publication Data

US 2016/0078618 A1 Mar. 17, 2016

Related U.S. Application Data

(63) Continuation of application No. PCT/JP2014/063988, filed on May 27, 2014.

(30) Foreign Application Priority Data

May 27, 2013 (JP) ................................. 2013-111073

(51) Int. Cl.
*G06T 7/00* (2017.01)
*A61B 6/00* (2006.01)
(Continued)

(52) U.S. Cl.
CPC .......... *G06T 7/0012* (2013.01); *A61B 5/0042* (2013.01); *A61B 5/0263* (2013.01);
(Continued)

(58) Field of Classification Search
CPC ... G06T 7/0012; A61B 5/0042; A61B 5/0263; A61B 5/02755; A61B 5/055; A61B 6/032; A61B 6/501; A61B 6/504; A61B 6/6211
See application file for complete search history.

(56) References Cited

U.S. PATENT DOCUMENTS

2005/0058331 A1 3/2005 Klotz
2010/0158337 A1* 6/2010 Burger ................. G06T 7/0014
382/131
(Continued)

FOREIGN PATENT DOCUMENTS

JP 2005-52648 3/2005
JP 2005-95340 4/2005
(Continued)

OTHER PUBLICATIONS

International Preliminary Report of Patentability and Written Opinion dated Dec. 10, 2015 in PCT/JP2014/063988 (English translation only).

(Continued)

*Primary Examiner* — Kim Vu
*Assistant Examiner* — Molly Delaney
(74) *Attorney, Agent, or Firm* — Oblon, McClelland, Maier & Neustadt, L.L.P.

(57) ABSTRACT

An image processing apparatus includes a processing circuitry. The processing circuitry acquires volume data including a blood vessel image. The processing circuitry generates volume data indicating a blood vessel image on a basis of the acquired volume data. The processing circuitry generates three-dimensional image data indicating a blood vessel image of a region corresponding to a predetermined dominance region of dominance regions, on a basis of the volume data indicating the blood vessel image.

10 Claims, 11 Drawing Sheets

(51) Int. Cl.
   *A61B 5/055*   (2006.01)
   *A61B 5/00*    (2006.01)
   *A61B 6/03*    (2006.01)
   *A61B 5/026*   (2006.01)
   *A61B 5/0275*  (2006.01)
   *A61B 8/06*    (2006.01)
   *G06T 15/08*   (2011.01)
   *A61B 8/08*    (2006.01)

(52) U.S. Cl.
   CPC .......... *A61B 5/02755* (2013.01); *A61B 5/055* (2013.01); *A61B 6/032* (2013.01); *A61B 6/501* (2013.01); *A61B 6/504* (2013.01); *A61B 6/5211* (2013.01); *A61B 8/06* (2013.01); *A61B 8/0808* (2013.01); *A61B 8/0891* (2013.01); *A61B 8/483* (2013.01); *A61B 8/5207* (2013.01); *G06T 7/0016* (2013.01); *G06T 15/08* (2013.01); *G06T 2200/04* (2013.01); *G06T 2207/10088* (2013.01); *G06T 2207/30016* (2013.01); *G06T 2207/30101* (2013.01)

(56) References Cited

U.S. PATENT DOCUMENTS

| | | | | |
|---|---|---|---|---|
| 2011/0103666 | A1* | 5/2011 | Ohishi | G06T 7/32 382/131 |
| 2012/0063663 | A1* | 3/2012 | Kawasaki | G06T 7/0014 382/133 |
| 2012/0263368 | A1 | 10/2012 | Nakano et al. | |
| 2013/0259336 | A1* | 10/2013 | Wakai | G06F 19/321 382/130 |

FOREIGN PATENT DOCUMENTS

| | | |
|---|---|---|
| JP | 2005-323994 | 11/2005 |
| JP | 2006-247388 | 9/2006 |
| JP | 2007-151881 | 6/2007 |
| JP | 2010-5456 | 1/2010 |
| JP | 2012-196436 | 10/2012 |
| JP | 2013-85652 | 5/2013 |

OTHER PUBLICATIONS

International Search Report dated Jul. 29, 2014, in PCT/JP2014/063988 filed May 27, 2014 (with English Translation).

Matthias Koenig et al., Quantitative Assessment of the Ischemic Brain by Means of Perfusion-Related Parameters Derived From Perfusion CT, Journal of the American Heart Association, Feb. 2001, 8 pages.

* cited by examiner

IMAGE PROCESSING APPARATUS AND IMAGE PROCESSING METHOD

CROSS-REFERENCE TO RELATED APPLICATION

This application is a Continuation Application of No. PCT/JP2014/63988, filed on May 27, 2014, and the PCT application is based upon and claims the benefit of priority from Japanese Patent Application No. 2013-111073, filed on May 27, 2013, the entire contents of which are incorporated herein by reference.

FIELD

The present embodiment as an aspect of the present invention relates to an image processing apparatus and an image processing method for observing the degree of ischemia.

BACKGROUND

Up to now, volume data in time phases is obtained by contrast-imaging and then continuously photographing various organs of an object using an image diagnostic apparatus such as an X-ray computed tomography (CT) apparatus, a magnetic resonance imaging (MRI) apparatus, and a nuclear medicine diagnostic apparatus, and a perfusion analysis on a blood flow is performed on the basis of the obtained volume data in the time phases. A conventional perfusion analysis is performed using data obtained by injecting a contrast medium or a tracer into an object. Such a perfusion analysis enables observation of a blood flow dynamic state.

A color map is used in many cases as a method of displaying results of a perfusion analysis. Observation using the color map is actively used to diagnose a blood flow dynamic state and an ischemia site.

In a case where a perfusion analysis is performed on the basis of volume data in time phases, a method of setting a region of interest (ROI) to a dominance region of each main blood vessel and obtaining an average value of blood flow rates is adoptable.

Unfortunately, according to the conventional color map as a method of displaying results of a perfusion analysis, a blood vessel image cannot be displayed for each dominance region, and a blood vessel image of a region corresponding to a dominance region desired to be observed cannot be presented. Accordingly, it is difficult for an operator to visually recognize a blood flow dynamic state when ischemia occurs. Moreover, according the method of setting a ROI to a dominance region of each main blood vessel, there is no choice but to randomly set a ROI concerning the dominance region of each main blood vessel on an image. Accordingly, an average value of blood flow rates obtained for the dominance region of each main blood vessel is not accurate and is low in precision.

BRIEF DESCRIPTION OF THE DRAWINGS

In accompanying drawings.

Figure 3A:
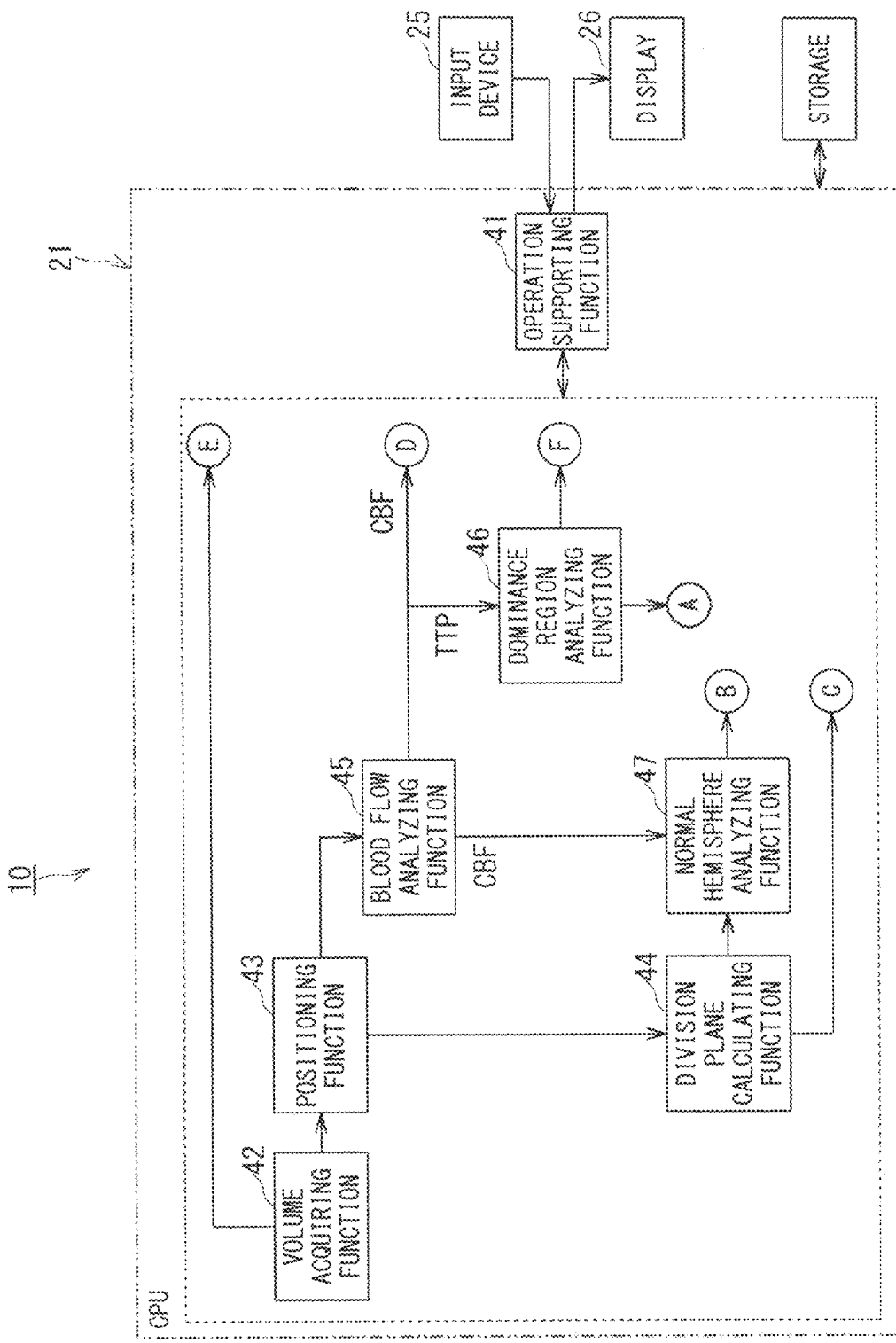
Figure 3B:
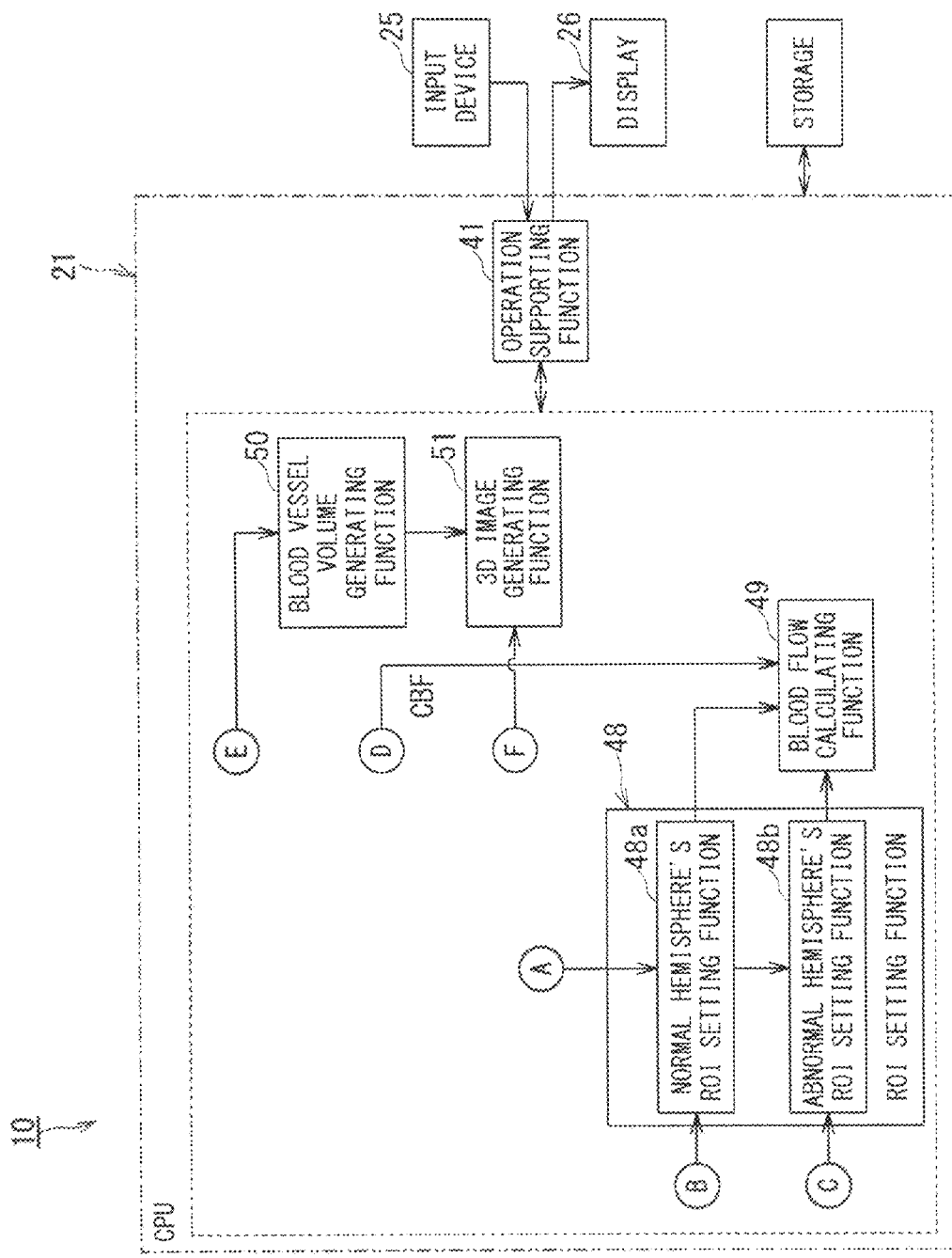
Figure 4:
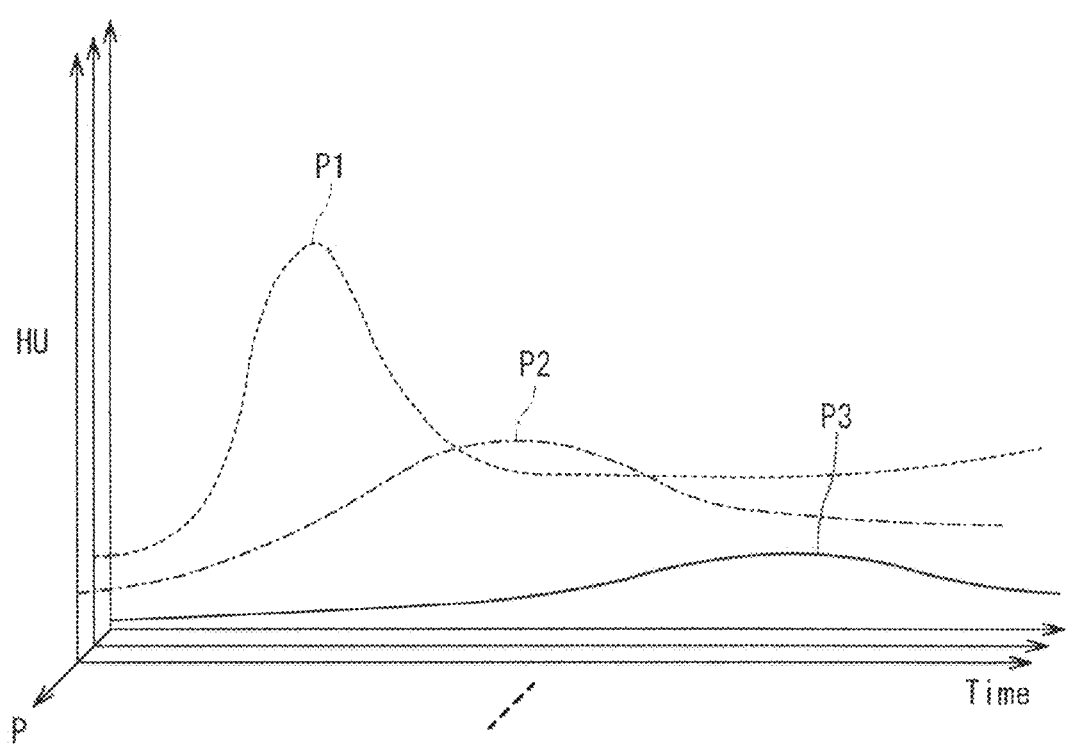
Figure 5:
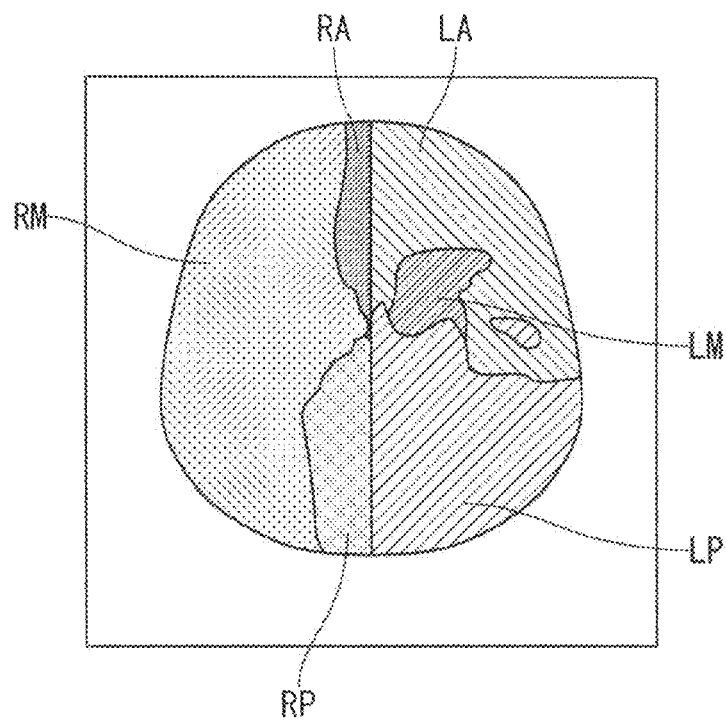
Figure 6:
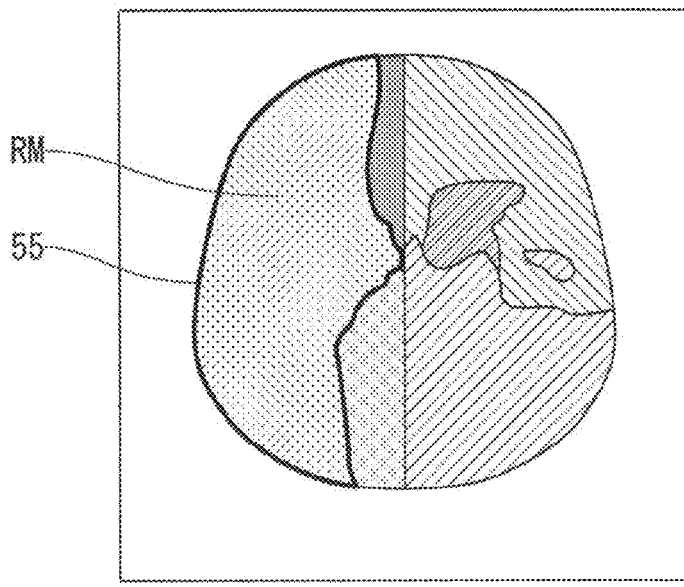
Figure 7:
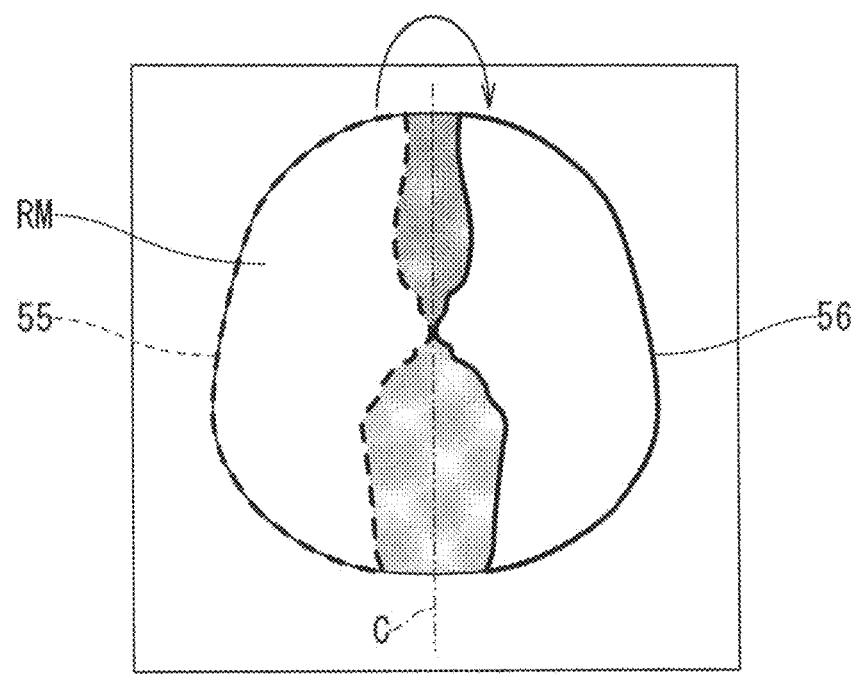
Figure 8:
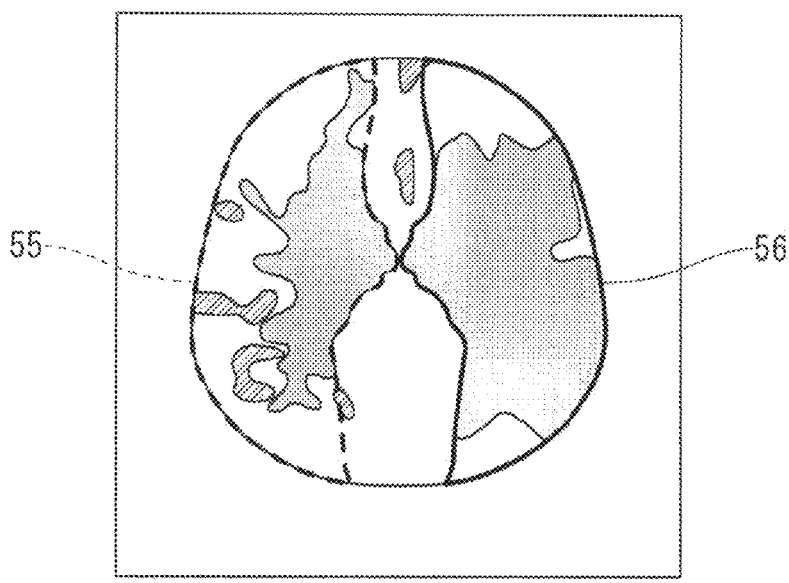
Figure 9:
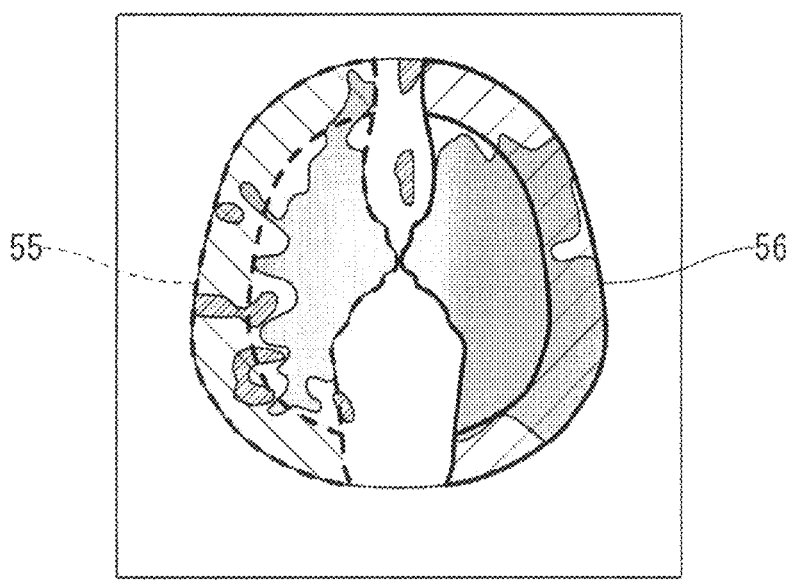
Figure 10:
Figure 11:
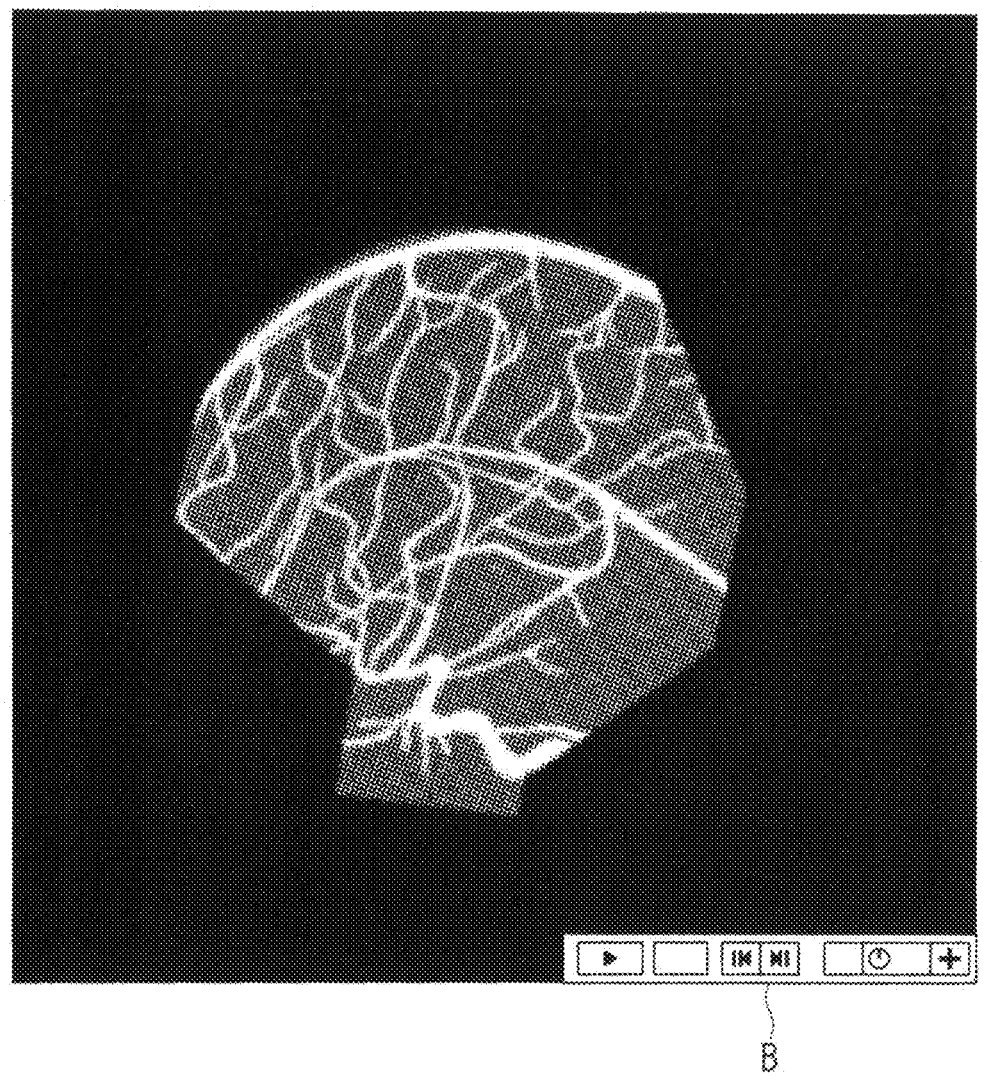
Figure 12:
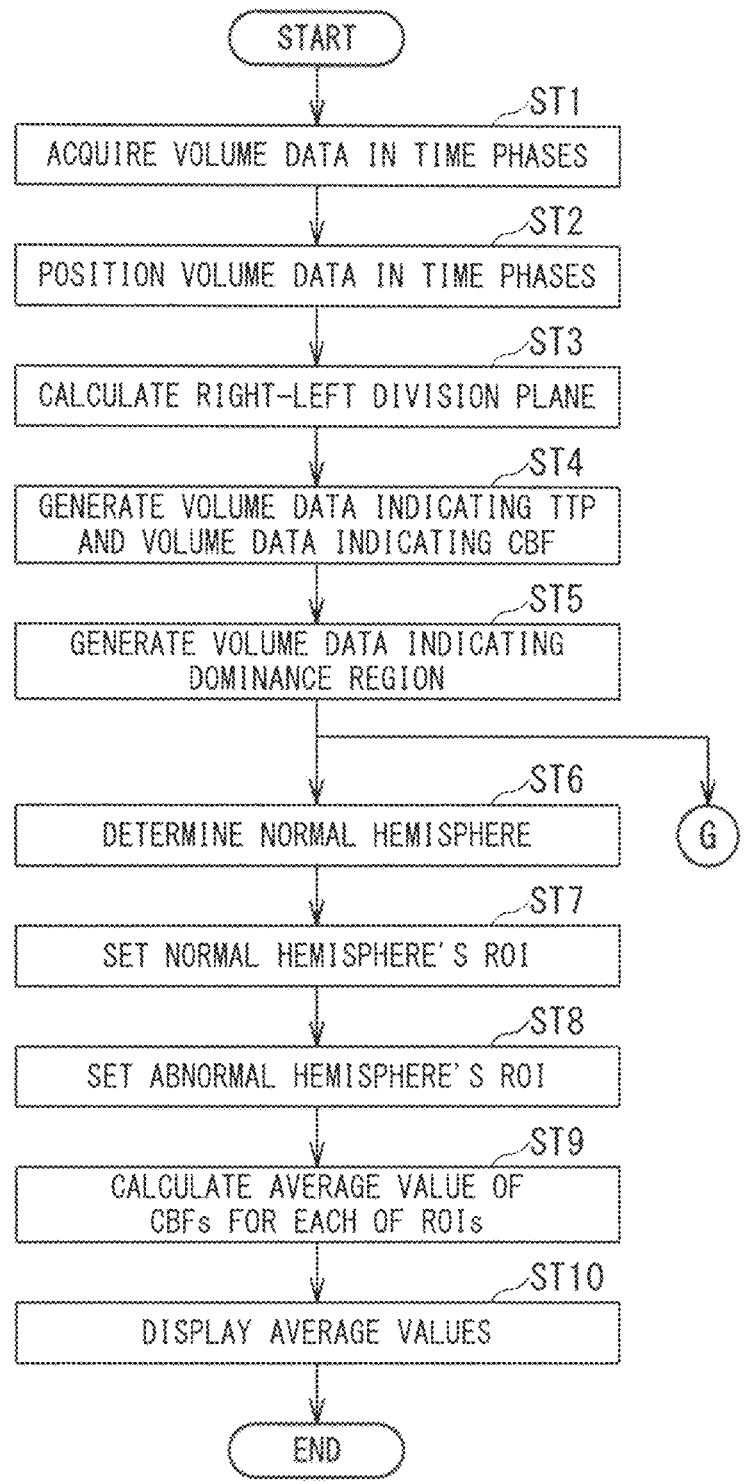
Figure 13:
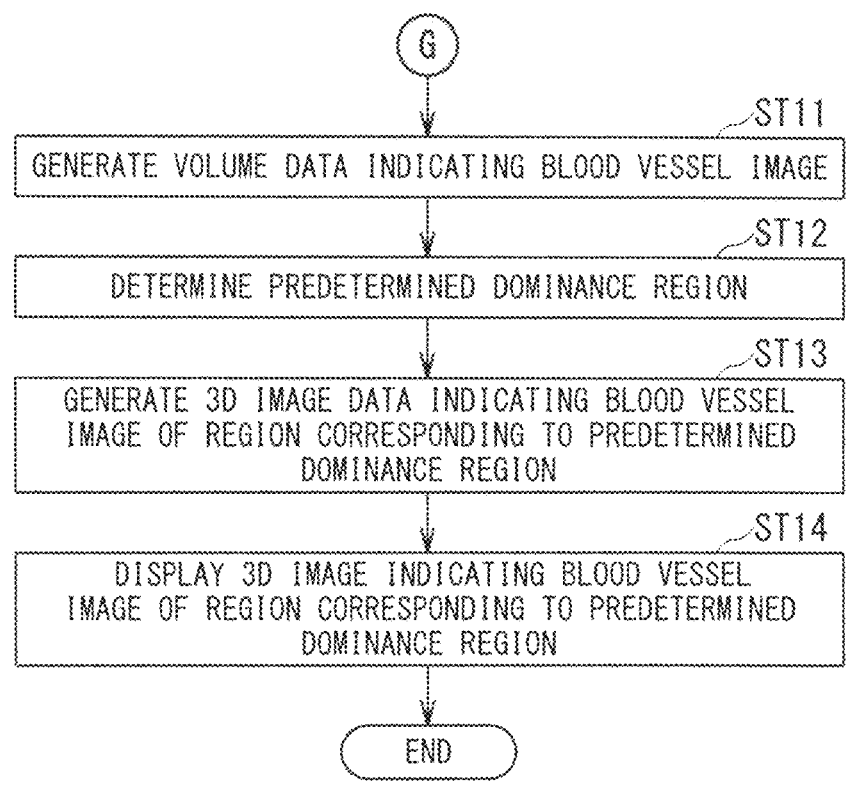

A set of FIGS. 3A and 3B is a block diagram showing functions of the image processing apparatus according to the present embodiment;

FIG. 4 is a diagram showing an example of TDC as a graph;

FIG. 5 is a diagram showing an example of a cross-sectional image based on volume data indicating a dominance region;

FIG. 6 is a diagram showing an example of a normal hemisphere's ROI concerning the dominance region of MCA, the normal hemisphere's ROI being set to a normal hemisphere;

FIG. 7 is a diagram showing an example of an abnormal hemisphere's ROI concerning the dominance region of MCA, the abnormal hemisphere's ROI being set to an abnormal hemisphere;

FIGS. 8 and 9 are diagrams each showing a cross-sectional image based on the volume data indicating CBF and the abnormal hemisphere's ROI;

FIG. 10 is a diagram showing a conventional display example of a three-dimensional image;

FIG. 11 is a diagram showing a display example of a three-dimensional image in the image processing apparatus according to the present embodiment; and FIGS. 12 and 13 are flowcharts each showing an operation of the image processing apparatus 10 according to the present embodiment.

DETAILED DESCRIPTION

An image processing apparatus and an image processing method according to the present embodiment are described with reference to the attached drawings.

To solve the above-described problems, the present embodiment provides the image processing apparatus, including a processing circuitry configured to: acquire volume data including a blood vessel image; generate volume data indicating a blood vessel image on a basis of the acquired volume data; and generate three-dimensional image data indicating a blood vessel image of a region corresponding to a predetermined dominance region of dominance regions, on a basis of the volume data indicating the blood vessel image.

To solve the above-described problems, the present embodiment provides the image processing method, including: acquiring volume data including a blood vessel image from a storage; generating volume data indicating a blood vessel image on a basis of the acquired volume data; generating three-dimensional image data indicating a blood vessel image of a region corresponding to a predetermined dominance region of dominance regions, on a basis of the volume data indicating the blood vessel image; and displaying the three-dimensional image data as a three-dimensional image on a display.

Figure 1:
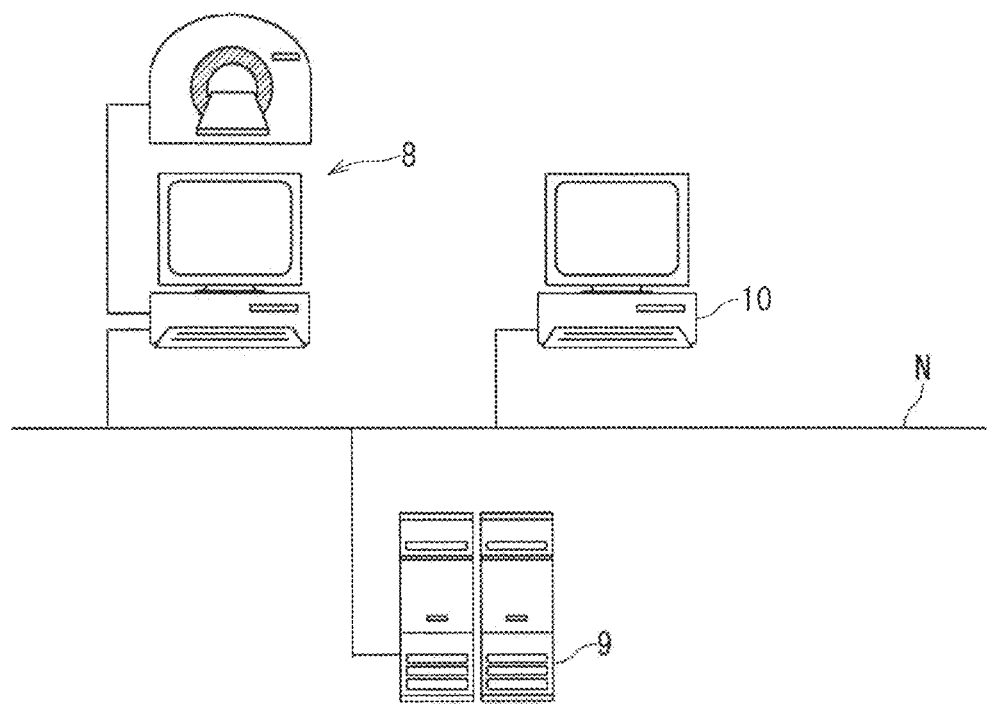
FIG. 1 is a schematic diagram showing a configuration of an image processing apparatus according to a present embodiment.

FIG. 1 is a schematic diagram showing a configuration of an image processing apparatus according to the present embodiment.

In FIG. 1, an image generating apparatus (modality) 8, an image managing apparatus (image server) 9, and an image processing apparatus (work station) 10 according to the present embodiment are provided. A plurality of the image processing apparatuses 10 may be provided.

Each of the image generating apparatus 8, the image managing apparatus 9, and the image processing apparatus 10 has a configuration based on a computer. The image generating apparatus 8, the image managing apparatus 9, and the image processing apparatus 10 are mutually communicably connected by a network N such as a local area network (LAN) of a hospital backbone. The image processing apparatus 10 does not necessarily need to be mutually communicably connected to the network N.

Examples of the image generating apparatus 8 include an ultrasonic diagnostic apparatus, an X-ray computed tomography (CT) apparatus, a magnetic resonance imaging (MRI) apparatus, and an angiographic apparatus, and, in general, the image generating apparatuses 8 are connected to the network N. The image generating apparatus 8 generates image data concerning an object such as an imaged site of a patient, in association with collateral information.

The image managing apparatus 9 is a database (DB) server that receives the image data generated by the image generating apparatus 8 via the network N and stores the received image data therein.

Figure 2:
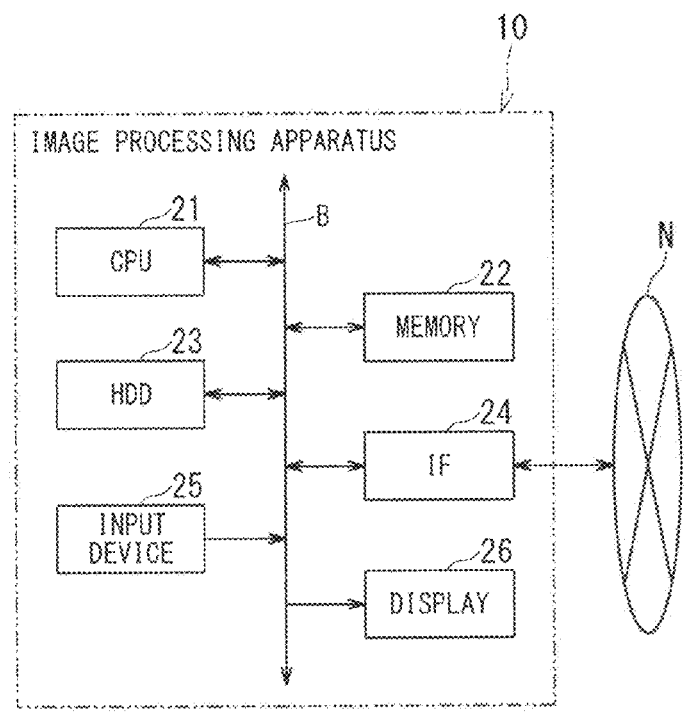
FIG. 2 is a diagram showing an example of a hardware configuration of the image processing apparatus according to the present embodiment.

FIG. 2 is a diagram showing an example of a hardware configuration of the image processing apparatus 10 according to the present embodiment.

In FIG. 2, which shows the hardware configuration of the image processing apparatus 10, the image processing apparatus 10 is roughly configured by basic hardware including a processing circuitry such as a CPU 21 as a processing circuitry, a memory 22, a hard disc drive (HDD) 23, an interface (IF) 24, an input device 25, and a display 26. The CPU 21 is mutually connected to each hardware element constituting the image processing apparatus 10, via a bus B as a common signal transmission line.

The processing circuitry means a special-purpose or general-purpose CPU or MPU (microprocessor unit) as well as an application specific integrated circuit (ASIC), programmable logic device, and the like. Examples of the programmable logic device include a simple programmable logic device (SPLD), a complex programmable logic device (CPLD), and a field programmable gate array (FPGA). Functions shown in a set of FIGS. 3A and 3B are implemented when the processing circuitry reads out and executes programs stored in memory 22 (or HDD 23) or directly incorporated in the processing circuitry.

Also, the processing circuitry may be made up of a single circuit or a combination of independent circuits. In the latter case, a memory may be provided for each of the independent circuits or a single memory may store programs corresponding to functions of the independent circuits.

The CPU 21 is a control device having a configuration of an integrated circuit (LSI) in which an electronic circuit made of semiconductor is sealed in a package having terminals. The CPU 21 executes programs stored in the memory 22. Alternatively, the CPU 21 has a function of loading, onto the memory 22, and executing programs stored in the HDD 23, programs that are transferred from the network N, received by the IF 24, and installed onto the HDD 23, and other programs.

The memory 22 is a storage including a read only memory (ROM) and a random access memory (RAM). The memory 22 has a function of: storing initial program loading (IPL), a basic input/output system (BIOS), and data; and being used as a working memory of the CPU 21 and a temporary storage of data.

The HDD 23 is a storage having a configuration in which a metal disk coated or deposited with a magnetic material is undetachably built in a readout device (not shown). The HDD 23 has a function of storing programs (including not only application programs but also an operating system (OS)) installed on the image processing apparatus 10 and various pieces of data.

The IF 24 includes a connector in conformity to parallel connection and serial connection. The IF 24 has a function of performing communication control suited to each standard and enabling connection to the network N through a telephone line, and this function enables the image processing apparatus 10 to be connected to the network N.

The input device 25 includes a keyboard and a mouse operable by a radiograph interpreter (operator) such as a doctor. An input signal generated in response to an operation on the input device 25 is sent to the CPU 21 via the bus B.

The display 26 includes a digital-to-analog (D/A) conversion circuit (not shown) and a monitor (not shown).

A set of FIGS. 3A and 3B is a block diagram showing functions of the image processing apparatus 10 according to the present embodiment.

When programs are executed by the CPU 21 (shown in FIG. 2), the image processing apparatus 10 functions as an operation supporting function 41, a volume acquiring function 42, a positioning function 43, a division plane calculating function 44, a blood flow analyzing function 45, a dominance region analyzing function 46, a normal hemisphere analyzing function 47, a ROI setting function 48, a blood flow calculating function 49, a blood vessel volume generating function 50, and a three-dimensional (3D) image generating function 51. Description is given of an example case where the functions 41 to 51 function in the form of software, but the entirety or a part of the functions 41 to 51 may be provided in the form of hardware in the image processing apparatus 10.

The operation supporting function 41 is an interface such as a graphical user interface (GUI) that mediates between: the functions 42 to 51; and the input device 25 and the display 26.

The volume acquiring function 42 has a function of acquiring, from the image managing apparatus 9, volume data (four-dimensional data) in time phases containing a blood vessel image with regard to a given patient. The volume data containing the blood vessel image may be obtained by continuous photographing (such as CT scan and MRI scan) after contrast imaging, and may be obtained by non-contrast imaging MR angiography (MRA). The volume acquiring function 42 can acquire volume data in time phases containing a brain, a heart, a liver, and other organs. Hereinafter, description is given of a case where volume the volume acquiring function 42 acquires data in time phases containing a whole brain.

The positioning function 43 has a function of positioning the volume data in the time phases acquired by the volume acquiring function 42. The positioning function 43 may make positions of multiple pieces of volume data in the second and subsequent time phases coincident with a position of the head volume data in the first time phase, of the volume data in the time phases.

The division plane calculating function 44 has a function of calculating a right-left division plane along which right and left hemispheres of the volume data in the time phases after the positioning by the positioning function 43 are to be divided. The division plane calculating function 44 may calculate the right-left division plane along which the right and left hemispheres are to be divided, using the head volume data in the first time phase of the volume data in the time phases after the positioning by the positioning function 43, and may apply the calculation result to multiple pieces of volume data in the second and subsequent time phases.

The blood flow analyzing function 45 has a function of: performing a blood flow analysis (perfusion analysis) on the basis of the volume data in the time phases after the positioning by the positioning function 43, to generate a time density curve (TDC) of a contrast medium; and generating volume data indicating a time to peak (TTP) and volume data indicating a cerebral blood flow (CBF) on the basis of the TDC.

FIG. 4 is a diagram showing an example of the TDC as a graph.

In the graph shown in FIG. 4, the vertical axis represents a CT value (Hounsfield unit: HU) corresponding to a density of a contrast medium injected into an object, and the horizontal axis represents time. Curves shown in FIG. 4 respectively represent TDCs at pixels P1 to P3.

In a perfusion analysis, a TDC is generated on the basis of a change in CT value, for each pixel P in volume data in time phases obtained by injecting a contrast medium or a tracer. Then, a TTP is calculated for each pixel P on the basis of the generated TDC. The volume data indicating the TTP may be displayed as a color map image with color coding based on each TTP value.

Returning to the description of the set of FIGS. 3A and 3B, the dominance region analyzing function 46 has a function of performing a dominance region analysis on a main blood vessel on the basis of the volume data indicating the TTP generated by the blood flow analyzing function 45 and generating volume data indicating a dominance region. Hereinafter, description is given of a case where an anterior cerebral artery (ACA), a posterior cerebral artery (PCA), and a middle cerebral artery (MCA) are adopted as main blood vessels.

FIG. 5 is a diagram showing an example of a cross-sectional image (territory map) based on the volume data indicating the dominance region.

As shown in FIG. 5, a whole brain is divided into two hemispheres (a left brain and a right brain) along the right-left division plane as a boundary. The left brain is divided into a dominance region LA of the ACA, a dominance region LP of the PCA, and a dominance region LM of the MCA. Similarly, the right brain is divided into a dominance region RA of the ACA, a dominance region RP of the PCA, and a dominance region RM of the MCA. In a case shown in FIG. 5, the left brain is an abnormal hemisphere, and the right brain is a normal hemisphere.

Returning to the description of the set of FIGS. 3A and 3B, the normal hemisphere analyzing function 47 has a function of obtaining a normal hemisphere of the two hemi-spheres on the basis of an average value of CBFs for each hemisphere divided by the division plane calculating function 44, based on the volume data indicating the CBF generated by the blood flow analyzing function 45. The normal hemisphere analyzing function 47 further has a function of determining, as a normal hemisphere, a hemisphere whose average value of CBFs is larger (whose TTP is shorter) while determining, as an abnormal hemisphere, a hemisphere whose average value of CBFs is smaller (whose TTP is longer).

The ROI setting function 48 has a function of setting a ROI concerning a dominance region on the basis of the volume data indicating the dominance region generated by the dominance region analyzing function 46. The ROI setting function 48 includes a normal hemisphere's ROI setting function 48a and an abnormal hemisphere's ROI setting function 48b.

The normal hemisphere's ROI setting function 48a of the ROI setting function 48 has a function of setting a normal hemisphere's ROI concerning a dominance region of a main blood vessel to the normal hemisphere determined by the normal hemisphere analyzing function 47, on the basis of the volume data indicating the dominance region of the main blood vessel generated by the dominance region analyzing function 46. The normal hemisphere's ROI setting function 48a defines, as the normal hemisphere's ROI, an outline of each of the dominance region of the ACA, the dominance region of the MCA, and the dominance region of the PCA in the normal hemisphere.

FIG. 6 is a diagram showing an example of the normal hemisphere's ROI concerning the dominance region of the MCA, the normal hemisphere's ROI being set to the normal hemisphere.

As shown in FIG. 6, the outline of the dominance region RM of the MCA in the right brain as the normal hemisphere is set as a normal hemisphere's ROI 55.

Returning to the description of the set of FIGS. 3A and 3B, the abnormal hemisphere's ROI setting function 48b of the ROI setting function 48 has a function of setting an abnormal hemisphere's ROI that is symmetrical to the normal hemisphere's ROI set by the normal hemisphere's ROI setting function 48a with respect to the right-left division plane calculated by the division plane calculating function 44.

FIG. 7 is a diagram showing an example of the abnormal hemisphere's ROI concerning the dominance region of the MCA, the abnormal hemisphere's ROI being set to the abnormal hemisphere.

As shown in FIG. 7, the normal hemisphere's ROI 55 is folded back symmetrically with respect to a right-left division plane C, whereby an outline of the dominance region LM of the MCA in the left brain as the abnormal hemisphere is created. Then, the created outline is set as an abnormal hemisphere's ROI 56. In FIG. 7, the dominance region RA of the ACA in the right brain, the dominance region RM of the MCA in the right brain, and the dominance region RP of the PCA in the right brain shown in FIG. 5 are folded back symmetrically with respect to the right-left division plane C.

Returning to the description of the set of FIGS. 3A and 3B, the blood flow calculating function 49 has a function of calculating an average value of CBFs for each of the normal hemisphere's ROI set by the normal hemisphere's ROI setting function 48a and the abnormal hemisphere's ROI set by the abnormal hemisphere's ROI setting function 48b, on the basis of the volume data indicating the CBF generated by the blood flow analyzing function 45. The average value of CBFs calculated by the blood flow calculating function 49 is displayed on the display 26 through the operation supporting function 41.

FIGS. 8 and 9 are diagrams each showing a cross-sectional image based on the volume data indicating the CBF and the abnormal hemisphere's ROI.

An average value of CBFs is calculated for each of portions inside of the normal hemisphere's ROI 55 and the abnormal hemisphere's ROI 56 shown in FIG. 8, of the cross-sectional image based on the volume data indicating the CBF. An average value of CBFs may be calculated for each of outer regions (shaded portions in FIG. 9) inside of the normal hemisphere's ROI 55 and the abnormal hemisphere's ROI 56.

Returning to the description of the set of FIGS. 3A and 3B, the blood vessel volume generating function 50 has a function of generating volume data indicating a blood vessel image according to a conventional technique, on the basis of at least one of the pieces of volume data in the time phases acquired by the volume acquiring function 42. Hereinafter, description is given of a case where the blood vessel volume generating function 50 generates volume data in one time phase indicating a blood vessel image, unless otherwise specified.

The 3D image generating function 51 has a function of generating three-dimensional image data in one time phase (such as multi planar reconstruction (MPR) image data and rendering image data) indicating a blood vessel image of a region corresponding to a predetermined dominance region of dominance regions, on the basis of the volume data in one time phase indicating the blood vessel image generated by the blood vessel volume generating function 50. The 3D image generating function 51 further has a function of displaying, as a three-dimensional image, the three-dimensional image data in one time phase indicating the blood vessel image of the region corresponding to the predetermined dominance region, on the display 26 through the operation supporting function 41.

In a case where the blood vessel volume generating function 50 generates volume data in time phases indicating a blood vessel image, the 3D image generating function 51 generates three-dimensional image data in time phases indicating a blood vessel image of a region corresponding to a predetermined dominance region. In this case, the 3D image generating function 51 can reproduce and display, as continuous three-dimensional images, the three-dimensional image data in the time phases indicating the blood vessel image of the region corresponding to the predetermined dominance region, on the display 26 through the operation supporting function 41.

Here, the region corresponding to the predetermined dominance region may be the predetermined dominance region itself, may be a region obtained by performing a dilation process on the predetermined dominance region, or may be a region obtained by performing an erosion process thereon. The predetermined dominance region may be a composite region formed by dominance regions of three or more dominance regions.

FIG. 10 is a diagram showing a conventional display example of a three-dimensional image.

As shown in FIG. 10, according to the conventional display of the three-dimensional image, a blood vessel image cannot be displayed for each dominance region, and a blood vessel image of a region corresponding to a dominance region desired to be observed cannot be presented. Accordingly, it is difficult for the operator to visually recognize a blood flow dynamic state when ischemia occurs.

Returning to the description of the set of FIGS. 3A and 3B, in the image processing apparatus 10 of the present embodiment, if the operator selects, through the input device 25, a desired position (pixel) on a cross-sectional image or a three-dimensional image (shown in FIG. 10) based on the volume data indicating the blood vessel image generated by the blood vessel volume generating function 50, the 3D image generating function 51 determines a dominance region corresponding to the selected pixel as a predetermined dominance region, from the volume data indicating the dominance region. Alternatively, if the operator selects, through the input device 25, a desired position (pixel) on a cross-sectional image (shown in FIG. 5) or a three-dimensional image based on the volume data indicating the dominance region generated by the dominance region analyzing function 46, the 3D image generating function 51 determines a dominance region corresponding to the selected pixel as a predetermined dominance region, from the volume data indicating the dominance region. Alternatively, if the operator selects (clicks), through the input device 25, a desired button on a display screen including buttons respectively representing the dominance regions based on the volume data indicating the dominance region generated by the dominance region analyzing function 46, the 3D image generating function 51 determines a dominance region corresponding to the selected button as a predetermined dominance region, from the volume data indicating the dominance region.

FIG. 11 is a diagram showing a display example of a three-dimensional image in the image processing apparatus 10 according to the present embodiment.

FIG. 11 shows: a three-dimensional image including a blood vessel image of a region corresponding to the dominance region LM or RM (shown in FIG. 5) of the MCA as the predetermined dominance region; or a three-dimensional image including a blood vessel image of a region corresponding to the ROI 55 or 56 (shown in FIG. 7) concerning the dominance region of the MCA as the predetermined dominance region. According to the display shown in FIG. 11, compared with the conventional display shown in FIG. 10, the operator can visually recognize a blood vessel image of a region corresponding to a dominance region desired to be observed that is selected on a blood vessel image, and thus can visually recognize a blood flow dynamic state when ischemia occurs.

A group of buttons B for receiving inputs of reproduction, stop, and other operations may be displayed on the display screen of the three-dimensional image shown in FIG. 11. In a case where the 3D image generating function 51 (shown in FIG. 3B) generates three-dimensional image data in time phases indicating a blood vessel image of a region corresponding to a predetermined dominance region, the three-dimensional image data in the time phases indicating the blood vessel image of the region corresponding to the predetermined dominance region can be reproduced and displayed as continuous three-dimensional images.

The blood flow analyzing function 45 may perform a blood flow analysis on each of N (for example, N=6) dominance regions on the basis of the volume data indicating the dominance region generated by the dominance region analyzing function 46, to generate volume data elements respectively indicating CBFs of the dominance regions, and may combine the volume data elements respectively indicating the CBFs of the dominance regions to generate the volume data indicating the CBF. In this case, the 3D image generating function 51 may generate three-dimensional image data of the volume data indicating the CBF.

Description is given on the assumption that the functions 41 to 51 shown in the set of FIGS. 3A and 3B are included in the image processing apparatus 10, but the entirety or a part of the functions 41 to 51 may be included in the image generating apparatus 8 or the image managing apparatus 9.

Next, an operation of the image processing apparatus 10 of the present embodiment is described with reference to FIG. 1, FIG. 12, and FIG. 13.

FIGS. 12 and 13 are flowcharts each showing an operation of the image processing apparatus 10 according to the present embodiment.

Description of the operation is started with reference to FIG. 12. The image processing apparatus 10 acquires, from the image managing apparatus 9, volume data in time phases obtained by contrast-imaging and then continuously photographing a whole brain of a given patient (Step ST1). The image processing apparatus 10 positions the volume data in the time phases acquired in Step ST1 (Step ST2). The image processing apparatus 10 calculates a right-left division plane along which right and left hemispheres of the volume data in the time phases after the positioning in Step ST2 are to be divided (Step ST3).

The image processing apparatus 10 performs a blood flow analysis on the basis of the volume data in the time phases after the positioning in Step ST2, to generate a TDC (shown in FIG. 4), and generates volume data indicating a TTP and volume data indicating a CBF on the basis of the TDC (Step ST4). The image processing apparatus 10 performs a dominance region analysis on each main blood vessel such as the ACA, the PCA, and the MCA on the basis of the volume data indicating the TTP generated in Step ST4, and generates volume data indicating a dominance region (shown in FIG. 5) (Step ST5).

The image processing apparatus 10 determines a normal hemisphere of the two hemispheres on the basis of an average value of CBFs for each hemisphere divided in Step ST3, based on the volume data indicating the CBF generated in Step ST4 (Step ST6). In Step ST6, the image processing apparatus 10 determines, as a normal hemisphere, a hemisphere whose average value of CBFs is larger while determining, as an abnormal hemisphere, a hemisphere whose average value of CBFs is smaller. The image processing apparatus 10 sets the normal hemisphere's ROI 55 (shown in FIG. 6) concerning a dominance region of a main blood vessel to the normal hemisphere determined in Step ST6, on the basis of the volume data indicating the dominance region of the main blood vessel generated in Step ST5 (Step ST7). The image processing apparatus 10 sets the abnormal hemisphere's ROI 56 (shown in FIG. 7) that is symmetrical to the normal hemisphere's ROI set in Step ST7 with respect to the right-left division plane calculated in Step ST3 (Step ST8).

The image processing apparatus 10 calculates an average value of CBFs for each of the normal hemisphere's ROI 55 (shown in FIG. 8) set in Step ST7 and the abnormal hemisphere's ROI 56 (shown in FIG. 8) set in Step ST8, on the basis of the volume data indicating the CBF generated in Step ST4 (Step ST9). The image processing apparatus 10 displays the average values calculated in Step ST9 on the display 26 (Step ST10).

The description of the operation is continued with reference to FIG. 13. The image processing apparatus 10 generates volume data indicating a blood vessel image according to a conventional technique, on the basis of volume data in one time phase of the volume data in the time phases acquired in Step ST1 (Step ST11). The image processing apparatus 10 determines a predetermined dominance region from the volume data indicating the dominance region generated in Step ST5 (Step ST12).

The image processing apparatus 10 generates three-dimensional image data in one time phase indicating a blood vessel image of a region corresponding to the predetermined dominance region determined in Step ST12, on the basis of the volume data in one time phase indicating the blood vessel image generated in Step ST11 (Step ST13). The image processing apparatus 10 displays, as a three-dimensional image (shown in FIG. 11), the three-dimensional image data in one time phase indicating the blood vessel image of the region corresponding to the predetermined dominance region, on the display 26 (shown in FIG. 2) (Step ST14).

According to the image processing apparatus 10 of the present embodiment, a blood vessel image of a region corresponding to a dominance region desired to be observed that is selected on a blood vessel image is presented to the operator, whereby the operator can visually recognize a blood flow dynamic state when ischemia occurs. Moreover, according to the image processing apparatus 10 of the present embodiment, a ROI suited to an actual dominance region of each blood vessel can be set, and an average value of blood flow rates obtained for the ROI concerning the dominance region of each blood vessel can be accurately calculated with high precision.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An image processing apparatus comprising:
processing circuitry configured to:
acquire volume data in time phases including a blood vessel image;
position the volume data in time phases;
perform a blood flow analysis on a basis of the volume data in time phases after the positioning thereby generating volume data of time to peak;
perform a dominance region analysis on a blood vessel on a basis of the volume data of time to peak, thereby generating volume data indicating a dominance region; and
generate three-dimensional image data indicating a blood vessel image of a region corresponding to a predetermined dominance region of dominance regions included in the volume data indicating the dominance region.

2. The image processing apparatus according to claim 1, wherein the processing circuitry is configured to define, as the region corresponding to the predetermined dominance region, one of: the predetermined dominance region itself; a region obtained by performing a dilation process on the predetermined dominance region; and a region obtained by performing an erosion process thereon.

3. The image processing apparatus according to claim 1, wherein the processing circuitry is configured to
perform the blood flow analysis, thereby generating not only the volume data of time to peak but also volume data indicating a blood flow rate.

4. The image processing apparatus according to claim 3, wherein the processing circuitry is configured to:
set a region of interest concerning the dominance region on a basis of the volume data indicating the dominance region; and
calculate an average value of blood flow rates for the region of interest, on a basis of the volume data indicating the blood flow rate.

5. The image processing apparatus according to claim 4, wherein the processing circuitry is configured to:
calculate a right-left division plane along which right and left hemispheres of the volume data in the time phases after the positioning are to be divided;
determine a normal hemisphere on a basis of an average value of blood flow rates for each divided hemisphere, based on the volume data indicating the blood flow rate;

set a normal hemisphere's region of interest concerning the dominance region to the normal hemisphere, on a basis of the volume data indicating the dominance region;

set an abnormal hemisphere's region of interest that is symmetrical to the normal hemisphere's region of interest with respect to the right-left division plane; and calculate an average value of blood flow rates for each of the normal hemisphere's region of interest and the abnormal hemisphere's region of interest.

6. The image processing apparatus according to claim 5, wherein the processing circuitry is configured to determine, as the normal hemisphere, a hemisphere whose average value of blood flow rates is larger.

7. The image processing apparatus according to claim 3, wherein the processing circuitry is configured to determine, when a position is selected using the volume data indicating the blood vessel image, a dominance region corresponding to the position as the predetermined dominance region, from the volume data indicating the dominance region.

8. The image processing apparatus according to claim 3, wherein the processing circuitry is configured to determine, when a position is selected using the volume data indicating the dominance region, a dominance region corresponding to the position as the predetermined dominance region, from the volume data indicating the dominance region.

9. The image processing apparatus according to claim 3, wherein the processing circuitry is configured to perform a blood flow analysis on each of the dominance regions on a basis of the volume data indicating the dominance region, to generate volume data elements respectively indicating blood flow rates of the dominance regions, and combine the volume data elements respectively indicating the blood flow rates of the dominance regions to generate the volume data indicating the blood flow rate.

10. An image processing method comprising:
acquiring volume data in time phases including a blood vessel image from a storage;
position the volume data in time phases;
perform a blood flow analysis on a basis of the volume data in time phases after the positioning thereby generating volume data of time to peak;
perform a dominance region analysis on a blood vessel on a basis of the volume data of time to peak, thereby generating volume data indicating a dominance region;
generating three-dimensional image data indicating a blood vessel image of a region corresponding to a predetermined dominance region of dominance regions included in the volume data indicating the dominance region; and
displaying the three-dimensional image data as a three-dimensional image on a display.

* * * * *